United States Patent [19]

Rinehart

[11] Patent Number: 4,532,813

[45] Date of Patent: Aug. 6, 1985

[54] KINETIC FLUID SAMPLER

[75] Inventor: Nerl D. Rinehart, Bakersfield, Calif.

[73] Assignee: Alpha Gauge & Instrument Company, Bakersfield, Calif.

[21] Appl. No.: 567,776

[22] Filed: Jan. 3, 1984

[51] Int. Cl.³ .............................................. G01N 1/14
[52] U.S. Cl. ................................. 73/863.02; 55/270; 73/863.11; 73/863.84
[58] Field of Search ................. 73/863, 863.01, 863.02, 73/863.03, 863.11, 863.84, 863.85, 883.86; 55/270

[56] References Cited

U.S. PATENT DOCUMENTS

| 2,452,143 | 10/1948 | Pellettere | 73/863.02 |
| 2,995,931 | 8/1961 | Perry et al. | 73/863.01 |
| 3,282,113 | 11/1966 | Sachnik | 73/863.02 |
| 4,037,475 | 7/1977 | Topham | 73/863.01 |

FOREIGN PATENT DOCUMENTS 104231  8/1981  Japan ............................... 73/863.01

Primary Examiner—Bernard Nozick
Attorney, Agent, or Firm—Dennis B. Haase

[57] ABSTRACT

The present invention is embodied in apparatus for the automatic periodic sampling of kinetic fluids wherein means are provided for tapping a conduit in which fluid is flowing to divert the samples of the fluid into a sampling plenum where each sample is accumulated under pressure and thereafter discharged into a collection vessel in which several samples may be accumulated under pressure for eventual testing. The invention contemplates the maintenance of each sample under pressure and isolated from foreign environments including ambient air, electrical discharge and the like, and further provides for a failure sensing means capable for detecting system failure and automatically shutting down the system and optionally signalling the failure so that immediate repairs can be effected, thereby minimizing downtime.

15 Claims, 4 Drawing Figures

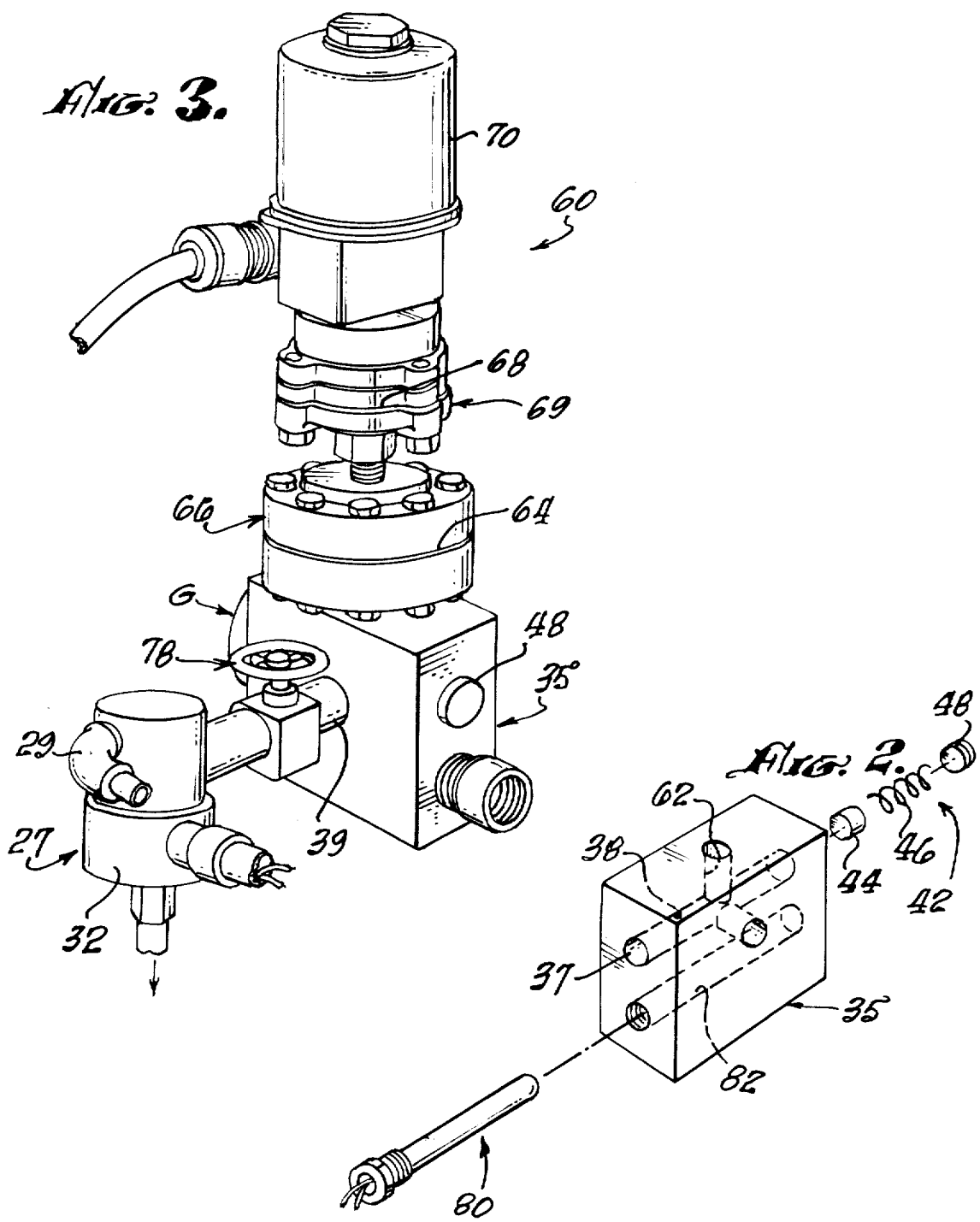

KINETIC FLUID SAMPLER

BACKGROUND OF THE INVENTION

In several industrial and commercial applications, the purchase and sale of fluid products typically occurs as a bulk transfer. Where relatively high volumes are involved, it is obviously impractical to package the fluid in containers and transfer it on that basis. Because of the impracticality of containerization, purchasers and sellers of fluids on such basis have determined that it is in their economic best interests to transfer such fluids in bulk and somehow effect a measurement of flow to determine the volume transferred and periodically sample the fluid for consistency and quality as the basis for the purchase and sale. As a consequence, a science has evolved about such commercial transactions which has as its root premise, the need to be able to accurately measure fluid volumes as the fluid continuously flows past a measuring point, and to obtain samples from which the makeup and quality of the fluid being transferred can be ascertained.

Examples of such transactions include volume users of combustible fuels such as commercial airports and military installations. In such instances, it is not uncommon for fuels to be piped into an installation directly from a refinery rather than to truck it in with tankers. Likewise, it has been a common practice for many years to buy and sell crude oil from a producing well by measuring the quantity of oil from the well as it flows through a pipeline, and at the same time, evaluating the quality of the crude to determine the price due the seller from the buyer at any particular point in time.

In the latter example, the quality of the crude is exceedingly important both to the buyer and the seller and the price to be paid is heavily dependent upon that quality. Crude pumped from a well will have a measurable specific gravity, and may often be polluted with certain emissible fluids such as water and undesirable salts. In order to ascertain the quality of bulk fluids flowing through a pipeline, the task facing the buyer is to extract periodic, essentially homogeneous, samples of the crude without interrupting flow and under such conditions as to reasonably assure the buyer that the sample extracted is representative. The seller, of course, has an equal interest in being assured that the sample extracted accurately reflects the gravity of the crude, which plays a major role in the price which he is to receive.

As will be described hereinafter the present invention addresses the problem of extracting accurate samples of a kinetic fluid flowing under significant pressures, and is uniquely capable of serving this vital interest in a very simple and inexpensive manner. More specifically, the present invention automatically collects and stores periodic samples of fluid under pressure in such a manner as to preserve the character and integrity of such samples for later testing.

Thus it is a primary objective of the present invention to periodically receive, segregate and store samples of fluid, such as crude oil, flowing under pressure in a pipeline, maintaining the fluid samples under pressure at all times until such time as the collected samples can be analyzed for whatever commercial purpose the buyer and/or seller deem appropriate.

Since many of the fluids sampled by the apparatus of the present invention are both volatile and flammable, it is a further objective to isolate and segregate fluid samples so as to avoid contact with oxygen and a potential source of ignition.

OVERVIEW OF THE PRIOR ART

Since the fluid to be sampled and analyzed is often flowing in significant volumes under great pressure, the collection of periodic samples poses several challenging problems. This is particularly true where the fluid is crude oil flowing through a pipe of substantial diameter from the wellhead owned by the bulk seller to either the refinery or a storage facility such as a tank farm owned and/or operated by the buyer. The crude is raised from the well under pressures generated both by the pumping unit and whatever internal hydrostatic pressures may be present. Depending upon how long the pipeline into which it is discharged is, additional pressure may be applied to the line to transmit the crude. The crude itself often contains water and salts which render it less desirable than pure crude. Likewise, the crude is of a specific gravity which will have a direct bearing on the price which the buyer will pay.

Because of the flows and pressures involved, it is obviously impractical to simply provide a petcock at some convenient location which can be periodically opened to obtain samples. Moreover, since samples may be required by the buyer to be relatively homogeneous and truly representative of the flow, and because the buyer may well require a sample after every ten barrels, it is obviously desirable to have some automatic means of obtaining and preserving those samples. Several early efforts to meet this vital need have been documented in prior patents, among them McKinney, et al. U.S. Pat. No. 2,636,387, Tapp, et al. U.S. Pat. No. 2,693,114, Hunter U.S. Pat No. 3,101,619, Sachnik U.S. Pat. No. 3,282,113, and more recently, Jiskoot U.S. Pat. No. 4,307,620. Common among the prior art efforts is the use of a pump to draw off fluid, take a sample of the fluid so drawn, and to return excess fluids to the pipeline. Such efforts are relatively primative and tend to avoid rather than utilize existing pressures available. Most prior devices are characterized by a highly complex plumbing arrangement, and do not, typically, isolate collected samples. None of those prior art arrangements perceived the unique advantages of receiving the samples under pressure and maintaining them isolated under such pressure until such time as they are analyzed. Other than a unity of purpose, i.e., the collection of fluid samples, prior devices have little if anything in common with the present invention.

DESCRIPTION OF THE DRAWINGS

With the foregoing as an introduction, a preferred embodiment of the invention will now be described in detail in conjunction with the drawings which accompany this application wherein:

FIG. 2 is an isometric view, partially sectioned, of the sampling block constructed in accordance with the present invention;

FIG. 3 is a schematic representation of the interrelationship of the sampler block, isolator and switching mechanism of the present invention.

DETAILED DESCRIPTION OF A PREFERRED EMBODIMENT

Figure 1:
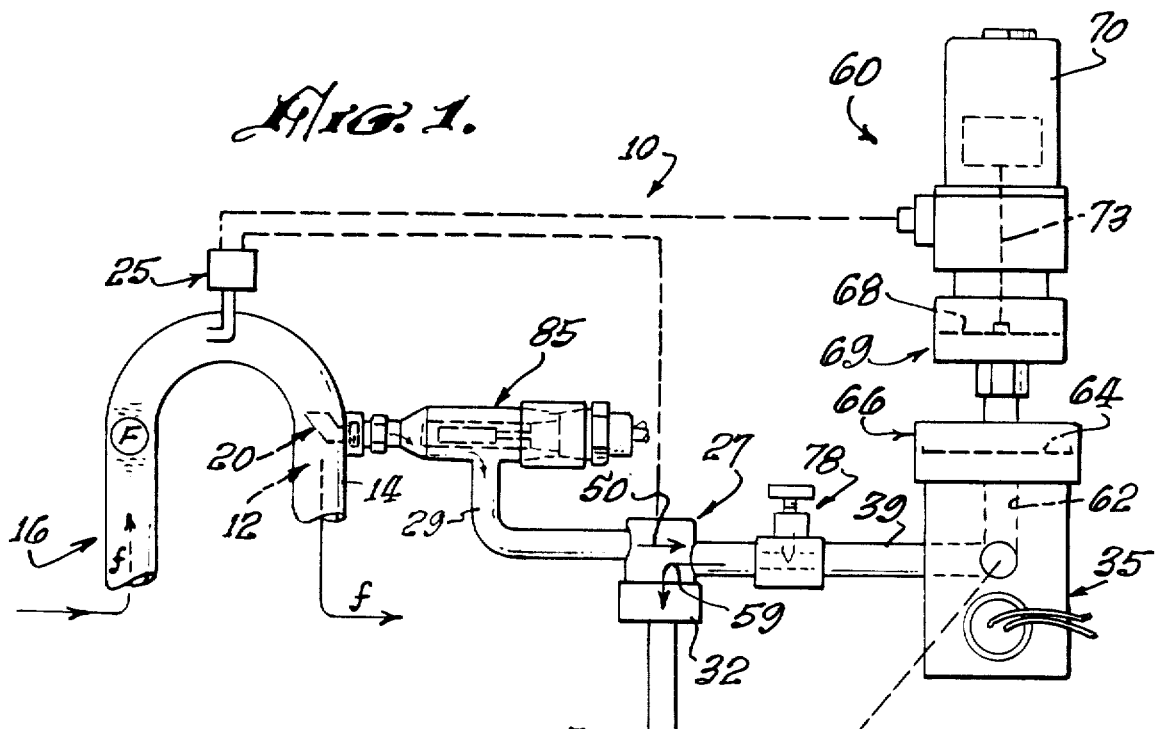
FIG. 1 is a schematic representation of an assemblage of component parts which, together, form apparatus for sampling fluids constructed in accordance with the present invention.

With reference now to the drawings, and with initial emphasis on FIG. 1, there is shown at (10) a kinetic fluid sampler device constructed in accordance with the present invention, to be pressure tight.

In order to permit extraction of fluid samples which will be representative of the fluid (F) flowing, the kinetic fluid sampler is provided with a fluid tap (12) which passes through a wall (14) of a fluid conduit or pipeline (16) so as to interject itself, at an appropriate angle, into the path of the fluid (F) flowing in the direction of the arrows (f).

In the embodiment used for illustrative purposes, the pipe (14) comprises one element of a LACT unit (Lease Automatic Custody Transfer) which is interposed in the transfer pipeline at the point where ownership of the fluid, in this instance, crude oil, is transferred from a well operator/seller to the buyer. The tap (12) terminates in a collector pipe (20) which is disposed at an approximate forty-five degree angle to the flow of the fluid, and in the middle of the stream. The collector pipe preferrably has an effective opening of approximately one-half of the inside diameter of the pipe (16) to thereby assure capture of a representative fluid sample.

The fluid sampler of the present invention must be capable of being cycled to collect periodic samples from time to time as may be determined by the buyer. For example, the buyer may require that a sample be taken at a particular frequency, such as every tenth barrel. Depending upon the velocity of flow and the diameter of the pipe, it will be apparent that cycling of the system might well take place at a relatively rapid frequency and it would be disproportionately expensive and time consuming to attempt to accomplish sampling by manually cycling the device. It is appropriate that cycling of the system be timed to occur on the basis of some predetermined measurable standard such as volumetric flow. It will be apparent that cycling based solely upon a timed sequence could be employed, although variations in line pressure and/or volumetric flow could result in undesirable sampling variations which would diminish the accuracy of the result, when a purely timed sequence is used. There are several well-known fluid flow measuring devices, any one of which would be effective for purposes of this invention and for that reason a fluid flow measuring device (25) is illustrated schematically as interposed in the stream of fluid (F). No particular import is attached to the specific details of the measuring device (25) other than it is to be disposed upstream of the fluid tap (12) so as to be in position to sense uninterrupted flow, and of course, that it be appropriately calibrated to provide the desired sequential cycling. The measuring device (25) typically includes means for transmitting a periodic signal at a frequency which is a function of volumetric flow.

An important aspect of the present invention is to provide a system for receiving, segregating and storing fluid samples collected at the tap (12). In order to do this the invention is equipped with means for rapidly directing fluid, in a predetermined sequence within the system. Accomplishment of this facet of the invention is attributed to a switching means, in this instance to a servo-motor operated three-way valve (27), cyclable to guide fluid samples collected through the fluid tap (12) within the sampler mechanism, as hereinafter described. To this end a collector line (29) interconnects the tap device (12) and the valve (27) to direct fluid samples extracted by the collector head (20) from the fluid (F) flowing in the conduit (14) to the valve. The valve (27) in the illustrated case is operated by a solenoid (32), although other known devices may be employed, which is wired to receive and act upon signals from the fluid flow measuring device (25). The simplest means of control, given the distance between the valve (27) and the measuring device (25) is, of course, electrical, although other modes of control are within the contemplation of the invention.

In accomplishing one of the many desirable objectives of the invention, each sample collected is controlled as to size and is, at all times, maintained isolated and discreet from contact with any foreign environment, including the atmosphere. This is accomplished in part, in accordance with the invention, by providing a sample accumulator block (35). With reference to FIG. 2, the block (35) is provided with a sample receiving port (37) of predetermined volume at the mouth of a sample receiving plenum (38) into which each sample passes via a feeder line (39) which interconnects the valve (27) with the port (37).

Because of the volatility of the fluid (F) it is highly desirable to maintain the fluid sample under pressure at all times. This feature also has been determined to result in the maintenance of a favorable specific gravity. In achieving this aspect of the invention the apparatus is designed to assure maintenance of each sample, once drawn, under a predetermined pressure. There is provided, for this purpose, a spring loaded piston assembly (42) at the remote end of the plenum (38). The assembly comprises a slidable piston member (44) which is preloaded by a spring (46), with the load on the spring being adjustable by an adjustment nut (48) which also holds the assembly in place in the bore (37).

It will now be seen that with the switchable valve (27) disposed in a receiving position to interconnect lines (29) and (39) as indicated by arrow (50) fluid within the pipe (16) will pass into the collector pipe (20) and through the collector line (29) into the line (39) where it will quickly accumulate in the sample plenum (38) under a significant increment of line pressure. A pressure gauge (G) may be installed so as to interfere with the fluid in the plenum (38). Since the fluid (F) is typically under significant pressure, the increment of time required to fill the lines and the sample port is small and is of a known duration. The fluid flow measuring device (25) is so constructed as to cycle the solenoid (32) to open the valve (27) to the plenum (38) for a predetermined duration, to thereby cause fluid flow in the direction of the arrow (50) for so long as is required to fill the port (37) with fluid at the predetermined desired pressure.

To this point in the operation of the device, it will be appreciated that the samples' integrity has been maintained at all times by assuring that the sample flows directly from the pipe (16) to the sample plenum (38). The sample having thus been accumulated in the plenum, to realize the potential of the device the sample must now be collected for testing without impairing its integrity. This is accomplished, in accordance with the invention, by providing a sample receiver in the form of a pressure vessel (55). The sample receiver is connected with the valve (27) by discharge line (57) so as to preclude the intrusion of air or other foreign substances. After the valve (27) has cycled to interconnect the collector pipe and the sample port for the predetermined time interval, it is again cycled by the solenoid by use of the timing mechanism of the fluid flow measuring device (25) to move the valve to a fluid discharge position thereby providing a flow in the direction as indicated by the arrow (59) to the sample receiver.

It will be remembered that one objective of the present invention is to periodically obtain and isolate discreet samples from the fluid flowing in the pipe (16) and to accumulate one or more such samples taken at intervals, under pressure, for eventual qualitative testing and determination of specific gravity. In keeping with this aspect of the invention, the sample receiver (55) is precharged, preferably with a pure inert gas such as, for example, helium. Any substance can be used which will not contaminate the fluid samples or mix with them to change their integrity. The charging pressure will be typically several pounds less than the pressure at which the collected sample in the sampler plenum is maintained and thus when the valve (27) is opened to permit flow in the direction of the arrow (59), the sample in the plenum (38) will pass directly to the vessel (55).

Figure 4:
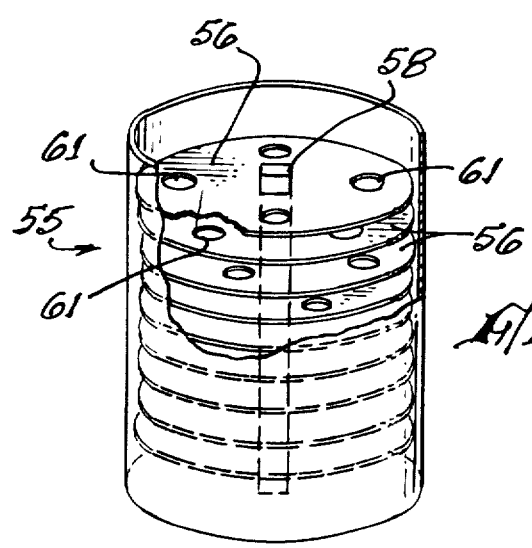
FIG. 4 is a sectional view of the container used for sample collection, showing the baffle system of the present invention.

With particular reference to FIG. 4, the interior of the container (55), there is provided, in accordance with this aspect of the invention a number of transverse baffle plates (56), each extending radially outwardly and supported on an axial rod (58) in serially spaced relation. Each plate (56) is punched to provide oil flow ports (61). In order to have the desirable effect of damping the interrelation of the oil samples and the changing gas as the containers fill, the ports are preferably misaligned to adjacent plates so as to form an interruption in the flow from plate to plate. The plates, so aligned, form gas retention shields from level to level as the accumulation of samples rises in the container. The suppression of gas bubbles results in a minimal loss of the lighter ends of the crude, thereby maintaining the integrity of the samples.

In order for the apparatus of the present invention to serve the purpose for which it is intended, it must reliably extract periodic samples and store them for testing. If the system should fail to cycle for any reason, it is essential that the failure be detected and promptly corrected. It is, therefore, an additional feature of the present invention to provide a failure detection system (60). The system (60), is of explosion proof construction and embodies both sensing and signalling means, hereinafter detailed. The system functions so that should the sampler system (10) fail at any point so that a sample is not accumulated in the sampler port (37) at the appropriate pressure, the system automatically shuts down and signals its failure. To accomplish this, the accumulater block (35) is provided with a failure sensing chamber (62) which communicates directly with the sample plenum (38). The signal chamber communicates directly with a diaphragm (64) housed in block (66). The diaphragm (64) is preferably of stainless steel to enhance the explosion proof character of the system. Pressure in the plenum (38) and failure sensing chamber (62) respectively will be substantially identical and will act upon the face of the diaphragm (64). Since pressures in these chambers are not insignificant and since it is an essential aspect of the invention that the fluid sample be maintained as isolated and discreet, a certain redundancy has been built into the failure detection system (60) to prevent inadvertent contact between the sample and the electrical signal mechanism. Thus, a second, backup diaphragm, (68) is disposed in series behind, or as depicted in FIGS. 1 and 3, above the diaphragm (64) and is interfaced by means of an incompressible fluid with the diaphragm (64) to sense deflection thereof in response to fluid pressure in the chamber. It is appreciated that interface between the diaphragm may also be accomplished by providing, by mechanical means or other means well-known in the art, between the two. Accordingly, should the diaphragm (64) rupture or by its failure, permit a portion of the sample to pass by or through the diaphragm, the sample will remain isolated from an electrical failure signal switch (70) by means of diaphragm (68) thereby preventing the possibility of inadvertent ignition of the flammable crude oil.

The backup diaphragm (68), of course, is linked in any known manner shown in (73) to the switch (70). Should the sample fail to come up to pressure for any reason, therefore, that failure would be sensed by the diaphragms and the switch (70) would respond by instantly shutting down the system and optionally providing a signal to the operator that the system has shut down.

In certain applications, it has been found desirable to be able to control the time rate of accumulation of the sample and this is accomplished, in accordance with the invention, by providing a throttle valve (78) of known construction in the feeder line (39). By adjustment of the throttle valve, of course, the time rate of accumulation of the sample can be readily controlled.

It is recognized in the art that crude oil viscosity is a function of its temperature as well as its parafin content, which varies considerably. If the crude is particularly cold, causing its viscosity to be very high, the time required to discharge the sample to the container (55) will be materially adversely affected. In order to overcome this problem, the invention contemplates the use of a heater assembly (80) disposed in a bore (82), spaced from and parallel with the plenum (38) within the block (35). The heater assembly may be a calrod or some other heater device which, when required, will raise the temperature in the sample chamber (38) sufficiently to permit the sample crude to flow quickly and uninhibited into the container (55).

Increased viscosity due to low temperature and parafin content has likewise been perceived as a problem in collecting the sample at the LACT unit. In order to minimize the deleterious effects of these factors, a preheater (85) may also be provided in the collector line (29) which preheats the sample in order to restore an appropriate time rate of flow. The construction of the preheater is well-known in the industry and it is not, therefore, necessary in the understanding of the invention to describe it in detail.

Having thus described a preferred embodiment of my invention, I claim:

1. Apparatus for collecting discrete samples of fluid flowing in a conduit under pressure comprising:
 a tap, said tap having a collector end thereof disposed in the fluid stream, said tap extending outwardly through the conduit wall;
 sampler means connected to said tap at a remote end thereof, said sampler means including a plenum into which fluid from said conduit flows under pressure and is accumulated to form a sample;
 collector means for receiving fluid samples;
 switchable valve means interposed in said tap intermediate said collector end and said sampler means, and interconnected with said collector means so as to selectively direct fluid samples into said collector means;

said switchable valve means being operable between a receiving position to provide a fluid connection between said collector end and said sampler means to thereby permit fluid from the conduit to flow into and accumulate in said sampler means and a discharge position so as to interconnect said sampler means and said collector means to form a discrete isolated fluid sample under a predetermined pressure;

means in said conduit upstream from said tap for measuring fluid flow including signal means for transmitting electrical impulses to said switchable valve means upon passage of a predetermined volume so as to cycle said switchable valve means between its receiving position and its discharge position so as to sequentially accumulate and thereafter discharge periodic fluid samples.

2. The apparatus as set forth in claim 1 wherein:
means is provided within said plenum for adjusting the volume of the sample collected therein.

3. The apparatus as set forth in claim 1 wherein:
said sampler means includes a heater for heating the fluid in said sampler.

4. The apparatus as set forth in claim 1 wherein:
a preheater is provided in said tap between a siphon end and said switchable valve means to preheat fluid from said conduit prior to receipt thereof in said sampler.

5. The apparatus as set forth in claim 1 wherein:
a throttle valve is disposed in said tap between said switchable valve means and said sampler means to control the rate of flow of fluid to said sampler means.

6. The apparatus as set forth in claim 1 wherein:
said collector means comprises a pressure vessel, a series of baffles transversely disposed in said pressure vessels in serial relation to one another, and each said baffle having several ports therein so as to permit the flow of fluid throughout said pressure vessel.

7. The apparatus as set forth in claim 6 wherein:
said ports in adjacent baffles are misaligned with respect to one another so as to provide a circuitous path for the flow of oil throughout said pressure vessel.

8. The apparatus as set forth in claim 1 wherein:
a failure detection system is provided, said failure detection system including a pressure sensing means connected with said plenum in said sampler means and signalling means interconnected with said fluid flow measuring means and operable to shut down said apparatus upon failure of the sample to accumulate in the plenum at adequate pressure, and to signal said failure.

9. The apparatus as set forth in claim 8 wherein:
said failure detection system being of explosion proof construction and including pressure sensing diaphragms in series and in fluid communication with said plenum and switch means interconnected with said diaphragms and said fluid measuring means, responsive to deflections of said diaphragms to shut down the apparatus upon failure thereof.

10. The apparatus as set forth in claim 8 wherein:
means is provided within said plenum for adjusting the volume of the sample collected therein.

11. The apparatus as set forth in claim 8 wherein:
said sampler means includes a heater for heating the fluid in said sampler.

12. The apparatus as set forth in claim 8 wherein:
a preheater is provided in said tap between a siphon end and said switchable valve means to preheat fluid from said conduit prior to receipt thereof in said sampler.

13. The apparatus as set forth in claim 8 wherein:
a throttle valve is disposed in said tap between said switchable valve means and said sampler means to control the rate of flow of fluid to said sampler means.

14. The apparatus as set forth in claim 8 wherein:
said collector means comprises a pressure vessel, a series of baffles transversely disposed in said pressure vessels in serial relation to one another, and each said baffle having several ports therein so as to permit the flow of fluid throughout said pressure vessel.

15. The apparatus as set forth in claim 14 wherein:
said ports in adjacent baffles are misaligned with respect to one another so as to provide a circuitous path for the flow of oil throughout said pressure vessel.

* * * * *